United States Patent [19]

Johnson

[11] 4,259,510
[45] Mar. 31, 1981

[54] PREPARATION OF TRIFLUOROMETHYLPHENYL NITROPHENYLETHERS

[75] Inventor: Wayne O. Johnson, Warminster, Pa.

[73] Assignee: Rohm and Haas Company, Philadelphia, PA

[21] Appl. No.: 150,788

[22] Filed: May 19, 1980

Related U.S. Application Data

[62] Division of Ser. No. 71,341, May 1, 1979.

[51] Int. Cl.³ .................. C07C 79/46; A01N 37/40
[52] U.S. Cl. .................. 560/21; 260/465 F; 260/465 E; 562/435; 562/438; 564/166; 568/585; 568/586; 568/775; 71/105; 71/108; 71/109; 71/116; 71/118; 71/124; 560/20
[58] Field of Search .................. 260/465 F, 465 E; 560/21; 562/435; 564/166; 568/586, 585

[56] References Cited

U.S. PATENT DOCUMENTS

| | | | |
|---|---|---|---|
| 2,489,423 | 11/1949 | Lawson et al. | 568/775 |
| 2,952,702 | 9/1960 | Galat | 568/778 |
| 3,536,767 | 10/1970 | Sommerfield | 568/770 |
| 3,726,929 | 4/1973 | Rayne | 568/778 |
| 3,772,344 | 11/1973 | Tarnow et al. | 260/456 P |
| 3,819,755 | 6/1974 | Tarnow et al. | 260/955 |
| 3,839,444 | 10/1974 | Theissen | 260/559 R |
| 3,904,695 | 9/1975 | Hendrickx et al. | 568/770 |
| 3,954,829 | 5/1976 | Rohe et al. | 260/465 F |
| 3,957,865 | 5/1976 | Rohe et al. | 71/98 |
| 4,017,300 | 4/1977 | Rohe et al. | 71/98 |
| 4,087,272 | 5/1978 | Rohe et al. | 71/120 |
| 4,094,913 | 6/1978 | Carlson | 568/778 |

OTHER PUBLICATIONS

McBee et al., J.A.C.S., 73, 1325-1326 (1951).
Lavagnino et al., Org. Preparations and Procedures International, vol. 9, pp. 96-98 (1977).
Mooradian et al., J.A.C.S., 73, 3470-3472 (1951).
Jones, J.A.C.S., 69, 2346-2350 (1947).

*Primary Examiner*—G. T. Breitenstein
*Attorney, Agent, or Firm*—Terence P. Strobaugh

[57] ABSTRACT

A process for preparing trifluoromethylphenyl nitro phenylethers which comprises treating a trifluoromethylhalobenzene with a base in a cosolvent system to afford a trifluoromethyl phenolate which may be isolated as its free phenol or reacted with an appropriately substituted halobenzene to afford a diphenylether herbicide or a precursor thereto.

12 Claims, No Drawings

PREPARATION OF TRIFLUOROMETHYLPHENYL NITROPHENYLETHERS

This is a division of application Ser. No. 071,341 filed May 1, 1979.

BACKGROUND OF THE INVENTION

This invention relates to a process for preparing known active nitro, trifluoromethyl containing diphenylether herbicides having the formula:

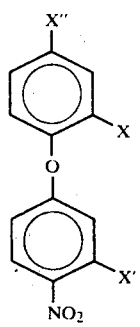

wherein X is hydrogen, halo such as chloro, bromo, fluoro and the like; trihalo lower alkyl such as trifluoromethyl and the like; lower alkyl such as methyl, ethyl, propyl, iso-propyl, n-butyl, sec-butyl, tert-butyl, and the like, X' is selected from hydrogen, halo, such as chloro, bromo, fluoro and the like, cyano, lower alkyl such as methyl, ethyl, n-propyl, n-butyl, sec-butyl, tert-butyl, n-pentyl and the like; lower alkoxy such as methoxy, ethoxy, iso-propoxy, butoxy, pentoxy and the like; carboxy; carbalkoxy such as carbomethoxy, carboethoxy, carbo-iso-propoxy, carbo-tert-butoxy, carbo-n-pentoxy, and the like; carbalkoxyalkoxy such as 1-carboethoxyethoxy, 1-carbomethoxypropoxy and the like; carbamoyl; mono- and di-lower alkyl substituted carbamoyl such as N-methylcarbamoyl, N-iso-propylcarbamoyl, N-n-butylcarbamoyl, N,N-dimethylcarbamoyl, N,N-diethylcarbamoyl and the like; substituted alkoxycarbonyl such as 2-methoxyethoxycarbonyl, 2-ethoxypropoxycarbonyl, 2-iso-butoxyethylcarbonyl and the like; alkenyloxycarbonyl such as 2-propenyloxycarbonyl, 2-(2-methylpropenyloxy)carbonyl and the like; or trifluoromethyl and X" is halo or trifluoromethyl with the proviso that when X" is halo X is trifluoromethyl.

The following U.S. patents disclose trifluoromethyl substituted diphenylethers U.S. Pat. Nos.: 3,798,276; 3,928,416; 4,031,131; 4,063,929; 3,784,635; 4,087,272; 4,002,662; 4,001,005; 3,983,168; 3,979,437; 3,941,830; 3,907,866; 3,873,302; 3,954,829; 3,839,444; 3,957,865; 4,017,300, and 3,862,209.

A key intermediate in the synthesis of the diphenyl ether (I, supra) is the substituted or unsubstituted trifluoromethylphenol. There are various routes to this compound. See for example U.S. Pat. Nos. 3,888,932; 3,772,344; 3,819,755 and references cited therein. The present processes either involve too many steps or are economically unattractive or both. [See Mooradian, et al., *J. Am. Chem. Soc.*, 73, 3470-2 (1951; McBee et al., *J. Am. Chem. Soc.*, 73, 1325-6 (1951); Jones, R. G., *J. Am. Chem. Soc.*, 69, 2346-50 (1947); and Lavagnino, E. R., et al., *Org. Preparations and Procedures International*, Vol. 9, pps 96-98 (1977).]

The basic problem in the preparation of a trifluoromethyl phenol is the sensitivity of the trifluoromethyl radical to not only concentrated but even dilute base. (See Jones, R. G., *J. American Chemical Society*, 69, 2346-50 (1947)).

It has now been discovered that by employing a special solvent system to regulate the amount of base in solution and reduce the presence of water, trifluoromethylphenates can be produced in a single step in good yield, in situ. The corresponding trifluoromethylphenols can be isolated upon acidification, or condensed directly with appropriately substituted halo nitrobenzenes to afford herbicidal diphenyl ethers or precursors thereof.

The following equation illustrates this process for preparing trifluoromethylphenol from a chloro substituted compound however, it is to understood that in place of the chloro radical, a fluoro radical could also be used;

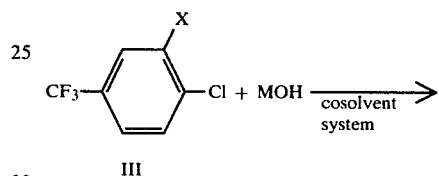

III

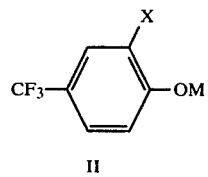

II wherein X is as defined above and M is a cation derived preferentially from an alkali metal or alternatively from an alkaline earth metal. Hydroxides such as sodium hydroxide, potassium hydroxide, calcium hydroxide, magnesium hydroxide, and the like may be employed with sodium being a preferred cation and potassium the most preferred cation. The reaction is conducted at a temperature in the range of from about 50° to about 100° C. and, preferably, in the range of from about 65° to about 85° C. for a period of time preferably in the range of from 5 hours to 5.5 days and most preferably in the range of from 10 to 55 hours. It is understood that some product is formed within several hours, however, the time periods set forth above represent the optimum time periods. The reaction is generally conducted at atmospheric pressure. Other halobenzenes (III, supra) include

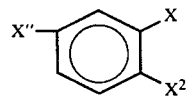

wherein X and X" are as defined above and $X^2$ is fluro or chloro.

A key element in this invention is the cosolvent system which is prepared from a dipolar, aprotic solvent and a non-nucleophilic, hydroxylated cosolvent.

Dipolar, aprotic solvents employed in this invention include solvents having dielectric constants in the range of from about 30 to about 70 which solvents are inert or substantially inert to the base employed. Examples of the preferred dipolar, aprotic solvents include dimethyl sulfoxide, tetrahydrothiophene-1,1-dioxide, hexamethylphosphoric triamide and the like.

The non-nucleophilic, hydroxylated cosolvent which provides for increased solubility of the metal hydroxide is believed to impart stability by hydrogen bonding with the formed 4-trifluoromethylphenolate salt.

Non-hindered alcohol such as methanol, ethanol, n-propanol or iso-propanol, however, may enter into competitive reactions with the 4-trifluoromethylphenolate resulting in formation of undesired by-products. Less nucleophilic n-alcohols ($C_4$ and above) are more desirable as cosolvents than the $C_1$-$C_3$ alcohols, listed above.

The hydroxylated cosolvents employed in this invention are those having the following structural formla:

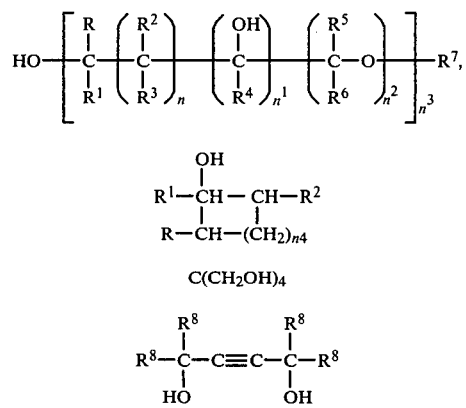

wherein R, $R^1$, $R^2$, $R^3$, $R^4$, $R^5$, $R^6$ and $R^7$ are the same or different groups selected from hydrogen; straight or branched lower alkyl, substituted or unsubstituted phenyl wherein the phenyl substituents may be alkyl, halo, lower alkoxy, or benzyl, and the like; $R^8$ is lower alkyl; n and $n^2$ are 0 or 1; $n^1$ is 0 to 2, $n^3$ is an integer of from 1 to 10; $n^4$ is 2 to 4 provided that $n^1$ is 2 only when n and $n^2$ are both 0, otherwise the sum of $n^1$ and $n^2$ may not be greater than 1; when $n^3$ is greater than 2, the sum of n and $n^2$ may not simultaneously be greater than 1 and $n^1$ must be 0; when $R^7$ is hydrogen, $n^1$ must be zero and the sum of n and $n^2$ must be 1 such that at least 3 of the groups R, R' plus either the pair $R^2$ and $R^3$ or the pair $R^5$ and $R^6$ must not be hydrogen.

Examples of the hydroxylated solvents include tert-butyl alcohol, pinacol, pentaerythritol, 2,4-dimethyl-2,4-pentanediol, 2,4-dimethyl-2,3,4-pentanetriol, 2,4-dimethyl-1,2-pentanediol, 2,4-dimethyl-3-pentanol, 2,2,4-trimethyl-3-pentanol, 2,2-dimethyl-1-propanol,

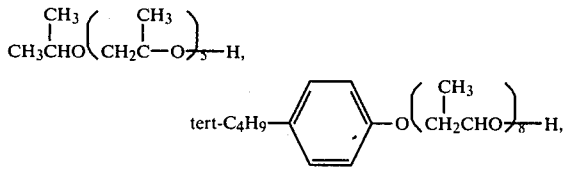

1-methyl-1-cyclohexanol, 2-iso-propyl-1-cyclopentanol and the like.

The cosolvents are employed at a ratio in the range of from about 1 to about 30 parts of the non-nucleophilic hydroxylated cosolvent to about 100 parts of the dipolar, aprotic solvent and preferably at a ratio in the range of from about 5 to about 20 parts of the non-nucleophilic solvent to about 100 parts of the dipolar, aprotic solvent.

The free phenol (II, below) may be isolated by treatment with acid or may be reacted with an appropriately substituted halobenzene to afford either a diphenyl ether herbicide or precursor which may be reacted further to afford the desired diphenyl ether (I, supra).

This procedure is illustrated by the following:

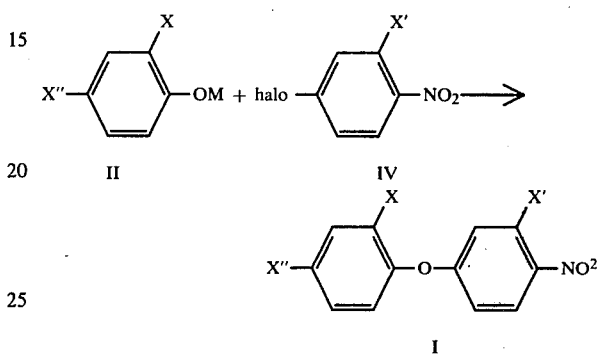

wherein M, X, X' and X" are as defined above and halo is preferably chloro or fluoro. Fluoro is preferred for enhancing reaction rates while chloro is preferred in terms of lower raw material costs.

The following illustrates in greater detail the preparation of the preferred diphenyl ether herbicides however, it is to be understood that other products falling within the generic description (I, supra) may also be prepared in a similar manner:

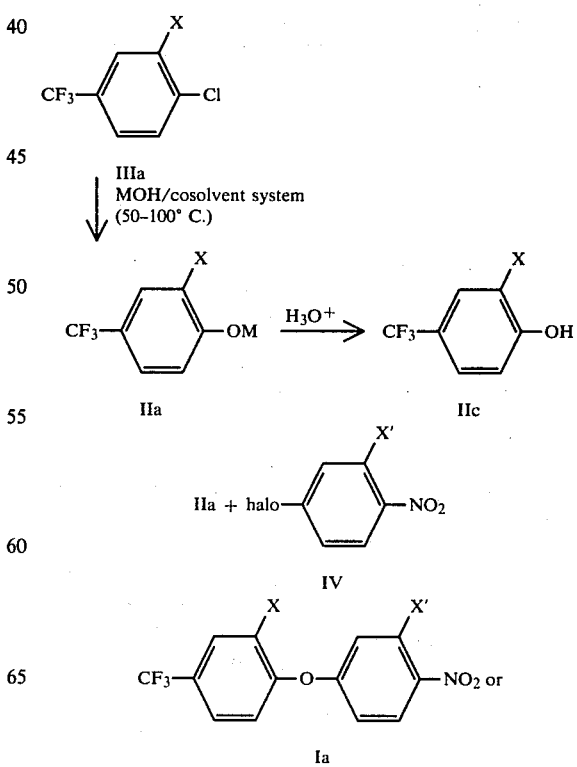

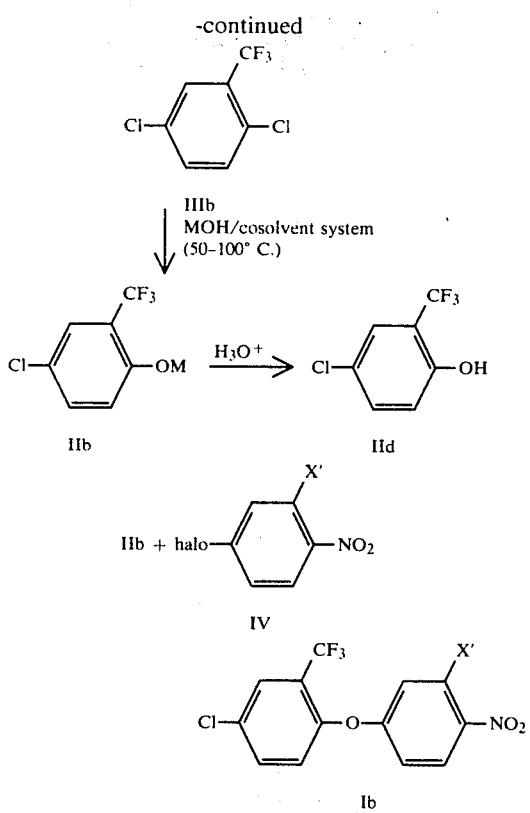

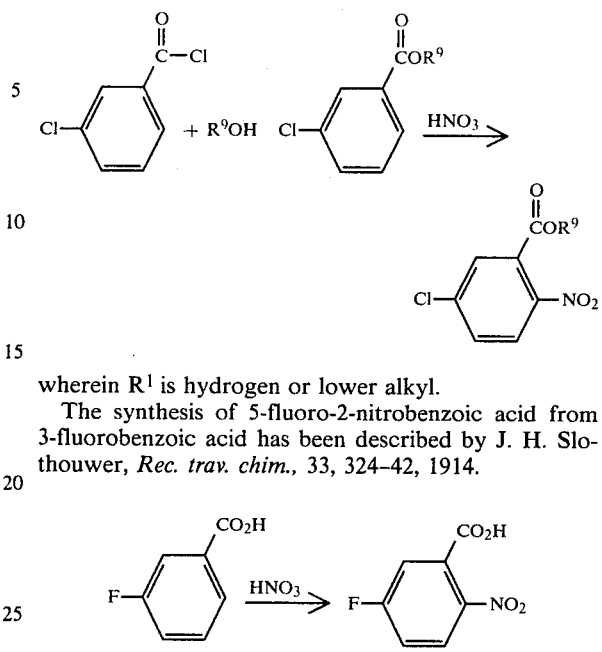

wherein $R^1$ is hydrogen or lower alkyl.

The synthesis of 5-fluoro-2-nitrobenzoic acid from 3-fluorobenzoic acid has been described by J. H. Slothouwer, *Rec. trav. chim.*, 33, 324–42, 1914.

The following examples illustrate the process of this invention but are not intended to limit the invention in any manner.

wherein X, X' and M are as defined above. Especially preferred are those compounds where X is hydrogen or chloro and $X^1$ is lower alkyl, lower alkenyl, or lower alkoxyalkyl esters or alkyl or dialkyl amides thereof. The lower alkyl esters can be readily hydrolyzed under acidic or basic conditions to afford the carboxylic acid which can readily be converted to alkali or alkaline earth metal salts or to various amine salts as desired.

The reaction between the trifluoromethylphenolate (II supra) and the halonitrobenzene (IV, supra) is generally conducted at a temperature in the range of from about 25° to 130° C. and preferably in the range of from about 25°–85° C. when the halo is fluoro and 60°–130° C., preferably 65°–85° C., when the halo is chloro. Dipolar, aprotic solvents which may be employed include dimethylsulfoxide, dimethylformamide, tetrahydrothiophene 1,1-dioxide, hexamethylphosphoric triamide, N-methylacetamide, ethylene carbonate, dimethoxy ethane, 1,4-dioxane and the like. Non-nucleophilic, hydroxylated cosolvents described above may advantageously be employed at 1–10 parts per 100 parts of the dipolar, aprotic solvent. If the free phenols (IIa or IId) are employed, the reaction must be conducted in the presence of an alkali metal or alkaline earth metal base such as anhydrous hydroxides, carbonates, bicarbonates and the like; preferred alkali metals are potassium and sodium.

Synthesis of 5-chloro-2-nitrobenzoates (i.e., X is carboxy) are described in Beilstein, IX, p. 401 and may be represented as follows:

EXAMPLE 1

2-Chloro-4-trifluoromethylphenol and potassium salt

To a flask equipped with a stirrer, thermometer, condenser and drying tube is added 3,4-dichlorobenzotrifluoride (21.5 g, 0.10 mole), potassium hydroxide pellets (85%, 0.20 mole) and dimethyl sulfoxide (100 ml). The reaction mixture is warmed to 65° C. for five hours during which time little reaction occurred. Tert-butyl alcohol (10 ml) is then added and the heating continued at 65° C. over the weekend. The reaction mixture is cooled, poured slowly onto ice (400 g), and extracted with toluene (100 ml, then 25 ml) to remove any unreacted starting material. To the yellow aqueous layer containing 2-chloro-4-trifluoromethylphenol, potassium salt (still cold) is added carbon tetrachloride (100 ml). The mixture is then acidified rapidly (pH 1) with conc. hydrochloric acid. The carbon tetrachloride layer is decanted, dried with anhydrous sodium sulfate and reduced under vacuum to afford 13.5 g of 2-chloro-4-trifluoromethylphenol Distillation at 3.0 mm, affords 10.8 g (69% yield) of substantially pure material, bp 79.5°–80.5° C. Elemental Anal. Calcd. for $C_7H_4ClF_3O$: C, 42.75; H, 2.06; Cl, 18.04; F, 29.00; Found: C, 43.01; H, 2.24; Cl, 17.28; F, 28.52.

EXAMPLE 2

2-Chloro-4-trifluoromethylphenol and potassium salt

To a flask equipped with a stirrer, thermometer, condenser and drying tube is added dimethyl sulfoxide (100 ml), powdered potassium hydroxide pellets (85%, 0.38 mole), 3,4-dichlorobenzotrifluoride (21.5 g, 0.10 mole) and pinacol (10 g). The reaction mixture is warmed at 75° C. for 52 hours, cooled and an aliquot analyzed by GLC to be 95% complete compared to unreacted 3,4-dichlorobenzotrifluoride. The product IIa (X=Cl) was isolated and used directly in Example 9B.

Variations of Example 1 used in the preparation of 2-chloro-4-trifluoromethylphenol are illlustrated in Table I:

TABLE I

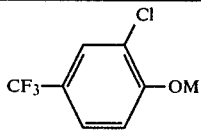

| Ex No. | Moles of III | Alkali Metal (Moles) | Non-Nucleophilic Cosolvent (ml) | Dipolar, Aprotic Solvent (ml) | Time (hrs) | Temp. °C. | Yield (%) |
|---|---|---|---|---|---|---|---|
| 3 | 0.1 | KOH (0.2) | tert-butanol (10) | DMSO (100) | 65 | 65 | 69 |
| 4 | 0.1 | KOH (0.48) | tert-butanol (20) | DMSO (100) | 132 | 65–75 | 73 |
| 5 | 0.1 | KOH (0.45) | tert-butanol (20) | DMSO (100) | 47 | 62–75 | 90 |
| 6 | 2.5 | KOH (8.76) | tert-butanol (500) | DMSO (2500) | 34 | 69–74 | 80 |
| 7 | 0.1 | KOH (0.2) | — | DMSO (100 ml) | 5 | 65 | 0 |

By following the general procedures of Examples 1 and 2,4-trifluoromethylphenol can generally be prepared from 4-chloro- or 4-fluorobenzotrifluoride. In addition, 2-trifluoromethylphenols can be prepared following the general procedures described in Examples 1 and 2, but employing 2-halo, halo being florine or chlorine, benzotrifluorides, a non-limiting example of which follows:

EXAMPLE 8

4-Chloro-2-trifluoromethylphenol

To a 300 ml, 3-necked flask fitted with a stirrer, condenser, thermometer and drying tube is added dimethylsulfoxide (100 ml), tert-butanol (20 ml), powdered potassium hydroxide (KOH) pellets (85%, 30 g) and 2,5-dichlorobenzotrifluoride (21.5 g, 0.10 mole). The reaction mixture is warmed to 71°–73° C. for 60 hours, then additional KOH (10 g) is added and heating is continued at 73°–75° C. for 24 hours. The reaction mixture is cooled and the solvent partially removed by distillation at 0.9 mm, bp 55° C.). The cooled pot residue is then poured into ice water (1000 g) which had been preacidified to pH 1 with conc. HCl (50 ml). The aqueous mixture is extracted with carbon tetrachloride (CCl4), the CCl4 layer decanted and dried and the solvent removed under vacuum to afford 10.8 g of 4-chloro-2-trifluoromethylphenol, which is sublimed to afford pure product, mp 81°–81.5° C. Elemental Anal. Calcd for C7H4ClF3O: C, 42.75; H, 2.06; Cl, 18.04: Found: C, 42.54; H, 2.36; Cl, 18.16.

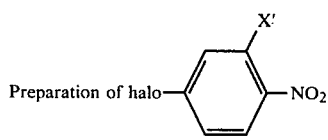

Preparation of halo

EXAMPLE 1A

Methyl 5-Chloro-2-nitrobenzoate

5-Chloro-2-nitrobenzoic acid (20.1 g,; 0.10 mol), is dissolved in anhydrous methanol (100 ml) and anhydrous hydrogen chloride gas is bubbled into the reaction mixture for 4 hours at room temperature. The reaction mixture is then poured into water and the aqueous mixture triturated with hexane, the hexane layer decanted, dried (anhd. MgSO4) and the solvent removed under vacuum to afford 11.7 g of methyl 5-chloro-2-nitrobenzoate, mp 50°–51° C.

EXAMPLE 2A

Methyl 3-Fluorobenzoate

To a solution of anhydrous hydrochloric acid (10.5 g) in anhydrous methanol (100 ml) is added m-fluorobenzoic acid (13.3 g.; 0.095 mole). The reaction mixture is stirred at room temperature overnight. The solvent and anhydrous hydrochloric acid are then removed under vacuum and the residue slurried with hexane (100 ml). The hexane insoluble layer is decanted and the hexane solution water washed (2×100 ml) before drying with anhydrous magnesium sulfate. The hexane filtrate is then concentrated under vacuum to afford 11.0 g (75% yield) of methyl 3-fluorobenzoate as a yellow liquid. Elemental anal. calcd. for C8H7FO2: C, 62.35; H, 4.57; F, 12.33. Found: C, 62.52; H, 4.70; F, 11.89.

EXAMPLE 3A

Methyl 3-Fluorobenzoate

To a 1-liter flask fitted with a stirrer, addition funnel, condenser, and drying tube containing diethyl ether (200 ml) and methanol (anhd.; 64 g,; 2.0 moles] is added dropwise m-fluorobenzoyl chloride (317 g,; 2.0 moles) at room temperature over a 3 hour period. Additional methanol (10 ml) is added and the reaction mixture is stirred at room temperature overnight. The reaction mixture is then filtered through a bed of silicic acid and the solvent removed under vacuum to afford 285 grams of methyl 3-fluorobenzoate (92.5% yield). This was identical to the product prepared in Example 2A.

By following substantially the procedure of Example 3A and by substituting for the methanol recited therein an equimolar quantitiy of another alcohol there may be obtained other desired esters. The following Table II taken together with the flow diagram illustrates this process:

TABLE II $$\text{F-C}_6\text{H}_4\text{-C(O)CL} + R^{10}\text{OH} \longrightarrow \text{F-C}_6\text{H}_4\text{-CO}_2R^{10}$$

| Ex No. | $R^{10}$ | Molecular Formula | Elemental Analysis | | |
|---|---|---|---|---|---|
| 4A | —$C_2H_5$ | $C_9H_9FO_2$ | — | | |
| 5A | —$CH_2CH_2N(CH_3)_2$ | $C_{11}H_{14}FNO_2$ | Calcd: | C, | 62.50; |
|   |   |   |   | H, | 6.70; |
|   |   |   |   | F, | 9.00; |
|   |   |   | Found: | C, | 62.25; |
|   |   |   |   | H, | 6.76; |
|   |   |   |   | F, | 8.48; |
| 6A | —$C_8H_{17}$ | $C_{15}H_{21}FO_2$ | Calcd: | C, | 71.40; |
|   |   |   |   | H, | 8.38; |
|   |   |   |   | F, | 7.52; |
|   |   |   | Found: | C, | 71.45; |
|   |   |   |   | H, | 8.57; |
|   |   |   |   | F, | 7.37; |
| 7A | —CH(CH$_3$)$_2$ | $C_{10}H_{10}FO_2$ | Calcd: | C, | 66.25; |
|   |   |   |   | H, | 5.57; |
|   |   |   |   | F, | 10.50; |
|   |   |   | Found: | C, | 65.88; |
|   |   |   |   | H, | 5.79; |
|   |   |   |   | F, | 10.13; |
| 8A | —$CH_2CH_2CH_2CH_3$ | $C_{11}H_{13}FO_2$ | — | | |
| 9A | —$CH_2CH_2OH$ | $C_9H_9FO_3$ | — | | |
| 10A | —$CH_2CH_2CH_3$ | $C_{10}H_{11}FO_2$ | — | | |
| 11A | —$CH_2CH_2OCH_3$ | $C_{10}H_{11}FO_3$ | — | | |

EXAMPLE 12A

N,N-Diethyl-3-fluorobenzamide

To a 50 ml flask fitted with a stirrer, condenser, drying tube and an addition funnel is added m-fluorobenzoyl chloride (15.9 g, 0.10 mole) and benzene (100 ml). Then a solution of diethylamine (14.6 g, 0.20 mole) in benzene (100 ml) is added dropwise over 1 hour and the reaction mixture allowed to stir at room temperature overnight. Water (150 ml) is then added rapidly and after trituration for a few minutes, the benzene layer is decanted and washed repeatedly with water (5×150 ml), dried (anhyd. $Na_2SO_4$) and the solvent removed under vacuum to afford 18 grams of N,N-diethyl-3-fluorobenzamide as a yellow oil. Elemental analysis calculated for $C_{11}H_{14}FNO$: C, 67.70; H, 7.22; F, 9.72; N, 7.16; Found: C, 66.40; H, 7.08; F, 9.65; N, 6.92.

EXAMPLE 13A

3-Fluorobenzamide

Into a stirred solution of m-fluorobenzoyl chloride (15.9 g, 0.10 mole) in benzene (200 ml) at 5° C. is bubbled anhydrous ammonia gas for 30 minutes. A white solid precipitates and the reaction mixture is allowed to stir at room temperature overnight. The white solid is removed by filtration and then triturated with water. The solid is dried to afford 10 g of m-fluoroenzamide, mp 130°–33° C. Elemental analysis calculated. for $C_7H_6FNO$: C, 60.40; H, 4.34; F, 13.66; N, 10.08. Found: C, 59.97; H, 4.43; F, 13.86; N, 10.39.

5-Fluoro-2-Nitrobenzoate Esters and Amides

By a modification of the method of Slothouwer, (supra) in which is described the preparation of 5-fluoro-2-nitrobenzoic by nitration of 3-fluorobenzoic acid, under standard nitration conditions the 3-fluorobenzoate esters and benzamides were nitrated as follows:

EXAMPLE 14A

Methyl 5-Fluoro-2-nitrobenzoate

To a 500 ml, 4-necked flask fitted with a stirrer, thermometer, addition funnel and reflux condenser is charged sulfuric acid (50 ml) and methyl m-fluorobenzoate (8.5 g, 0.055 mole). The reaction mixture is then cooled to 5° C. and a solution of potassium nitrate (reagent 5.57 g, 0.055 mole) is concentrated sulfuric acid (50 ml) is added dropwise over a 30 minute period. Ten minutes after completion of addition the reaction mixture is poured onto 500 g of cracked ice and the product extracted into benzene (3×100 ml). The combined benzene extracts are dried with anhydrous magnesium sulfate and the filtrate reduced in vacuo to give 10.6 g (96%) of product, which is a yellow liquid. Anal. Calcd. for $C_8H_6FNO_4$: C, 48.20; H, 3.04; F, 9.54; N, 7.02. Found: C, 50.15; H, 3.34; F, 9.17; N, 6.77.

By following substantially the procedure of Example 14A and by substituting an appropriate ester or amide of 3-fluorobenzoic acid for the ester recited therein the products depicted in Table III may be prepared.

TABLE III $$\text{F-C}_6\text{H}_3(\text{NO}_2)\text{-C(O)-}R^{11}$$

| Ex No. | $R^{11}$ | Molecular Formula | Elemental Analysis | | |
|---|---|---|---|---|---|
| 15A | —OH | $C_7H_4NO_4$ | Calcd: | C, | 45.40; |
|   |   |   |   | H, | 2.18; |
|   |   |   |   | F, | 10.25; |
|   |   |   | Found: | C, | 45.02; |
|   |   |   |   | H, | 2.13; |
|   |   |   |   | F, | 9.84; |
| 16A | —$OC_2H_5$ | $C_9H_8FNO_4$ | — | | |
| 17A | —$OC_8H_{17}$ | $C_{15}H_{20}FO_4$ | Calcd: | C, | 60.60; |
|   |   |   |   | H, | 6.78; |
|   |   |   |   | F, | 6.40; |
|   |   |   | Found: | C, | 63.10; |
|   |   |   |   | H, | 7.08; |
|   |   |   |   | F, | 6.50; |
| 18A | —$N(C_2H_5)_2$ | $C_{11}H_{13}FN_2O_3$ | Calcd: | C, | 55.00; |
|   |   |   |   | H, | 5.45; |
|   |   |   |   | F, | 7.90; |
|   |   |   | Found: | C, | 54.89; |
|   |   |   |   | H, | 5.46; |
|   |   |   |   | F, | 7.82; |
| 19A | —OCH(CH$_3$)$_2$ | $C_{10}H_9FNO_4$ | — | | |
| 20A | —$NH_2$ | $C_7H_5FN_2O_3$ | — | | |
| 21A | —$O(CH_2)_3CH_3$ | $C_{11}H_{12}NO_4$ | — | | |
| 22A | —$OCH_2CH_2CH_3$ | $C_{10}H_{10}FNO_4$ | Calcd: | C, | 52.86; |
|   |   |   |   | H, | 4.43; |
|   |   |   |   | F, | 6.16; |
|   |   |   | Found: | C, | 53.34; |
|   |   |   |   | H, | 4.40; |
|   |   |   |   | F, | 5.97; |
| 23A | —$OCH_2CH_2OCH_3$ | $C_{10}H_{10}FNO_5$ | Calcd: | C, | 49.58; |
|   |   |   |   | H, | 4.14; |
|   |   |   |   | F, | 5.75; |
|   |   |   | Found: | C, | 49.57; |
|   |   |   |   | H, | 4.00; |
|   |   |   |   | F, | 5.85; |
| 24A | —$OCH_2CH_2OH$ | $C_9H_8FNO_5$ | Calcd: | C, | 47.37; |
|   |   |   |   | H, | 3.53; |
|   |   |   |   | F, | 7.91; |
|   |   |   | Found: | C, | 47.53; |
|   |   |   |   | H, | 3.74; |
|   |   |   |   | F, | 7.73; |

EXAMPLE 25A

Ethyl 2-(5-Fluoro-2-nitrophenoxy)propionate 2,4-Difluoronitrobenzene (16.9 g; 0.10 mole), ethyl lactate (11.8 g; 0.10 mole), and anhydrous potassium carbonate (13.8 g, 0.10 mole) are combined in dioxane (200 ml) and the temperature is brought to 95° C. over a 1.5 hour period and maintained at 95° C. for 3 hours. The reaction mixture is cooled to room temperature, the inorganic solids removed by filtration and the solvent removed under vacuum to afford a dark colored oil, from which low boiling fractions are removed by distillation (bp., 79° C./0.5 mm). The pot residue is then cooled to afford 15.9 g of crude product, which is recrystallized from ligroin/acetone to afford ethyl 2-(5-fluoro-2-nitrophenoxy)propionate as yellow needles, m.p. 64°–65° C. Elemental anal. Calcd for $C_{11}H_{12}FNO_5$: C, 51.4; H, 4.70; F, 7.38; N, 5.45. Found: C, 51.35; H, 4.74; F, 7.60; N, 5.44.

EXAMPLE 26A

2-Ethoxy-4-fluoronitrobenzene

To a solution of anhydrous sodium ethoxide (0.55 mole) [prepared by dissolving sodium metal (12.6 g, 0.55 mole) in anhydrous ethanol (300 ml)] at 0° C. is added 2,4-difluoronitrobenzene (79.5 g, 0.50 mole) dropwise over an 8 hour period. Upon completion of addition the reaction mixture is allowed to warm to room temperature and stirred overnight. The solid is removed by filtration, and triturated with toluene and water. The toluene extract is combined with the original filtrate, dried with anhydrous sodium sulfate and the solvent is removed under vacuum to afford 218 g of a yellow oil which was distilled at 0.3 mm, b.p. 95°–98° C. to afford substantially pure 2-ethoxy-4-fluoronitrobenzene.

Preparation of 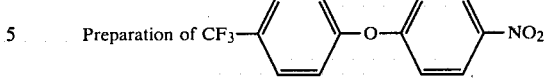

EXAMPLE 1B

Methyl 5(2-chloro-4-trifluoromethylphenoxy)2-nitrobenzoate

To a 5-liter, 4-necked flask fitted with a stirrer, thermometer, addition funnel, reflux condenser and drying tube is added dimethyl sulfoxide (200 ml), 2-chloro-4-trifluoromethylphenol (715 g, 3.64 mole), and anhydrous potassium carbonate (520 g, 3.72 moles). The reaction mixture is stirred at room temperature overnight under a nitrogen atmosphere. Then methyl 5-fluoro-2-nitrobenzoate (724 g, 3.64 moles) is added over a 1 hour period (slight exotherm to 31° C.). After stirring overnight at room temperature, the inorganic solids are removed by filtration and 1700 ml of dimethyl sulfoxide removed under vacuum (1 mm, pot temp. of 85° C., vapor temp. of −40° C.). The residue is diluted with a large volume of carbon tetrachloride and water washed. The organic layer is dried with anhydrous magnesium sulfate and the solvent removed under vacuum to afford 1142 g of methyl 5-(2-chloro-4-trifluoromethylphenoxy)-2-nitrobenzoate (84% yield). Anal. Calcd. for $C_{15}H_9ClF_3NO_5$: C, 47.90; H, 2.42; Cl, 9.45; F, 15.20; N, 3.73. Found: C, 47.83; H, 2.47; Cl, 9.15; L F, 14.84; N, 3.69.

By following the procedure of Example 1B and by varying temperature, time and solvent a repeat was made of the methyl ester. Also prepared was the ethyl ester and several other esters. The following Table IV illustrates this process.

TABLE IV $$CF_3-\phantom{x}\overset{Cl}{\bigcirc}-OH + F-\overset{COR^{11}}{\bigcirc}-NO_2 \xrightarrow{K_2CO_3} CF_3-\overset{Cl}{\bigcirc}-O-\overset{COR^{11}}{\bigcirc}-NO_2$$

| Example No. | $R^{11}$ | Time (hours) | Temp (°C.) | Solvent | Yield (%) |
|---|---|---|---|---|---|
| 2B | —OH | 8 | 70–100 | DMSO | 1 |
| 3B | —OCH₃ | 1 | 70 | DMSO | 30 |
| 4B | —OCH₃ | 8 | reflux | dioxane | 10 |
| 5B | —OCH₃ | 48 | 25 | DMSO | 87 |
| 6B | —OCH₃ | 5 | 25 | DMSO | 84 |
| 7B | —OCH₃ | 8 | 25–48 | DMSO | 77 |
| 8B | —OC₂H₅ | 24 | 25 | DMSO | 68 |
| 9B | —OC₂H₅ | 72 | 25–70 | DMSO | 86 |
| 10B | —OC₂H₅ | 8 | 40 | DMSO | 90 |
| 11B | —OC₃H₇n | 24 | 25 | DMSO | 88 |
| 12B | —OC₃H₇iso | 96 | 25 | DMSO | 55 |
| 13B | —OC₄H₉n | 72 | 25 | DMSO | 81 |
| 14B | —OC₈H₁₇-n | 72 | 25 | DMSO | 48 |
| 15B | —OCH₂CH₂OH | 24 | 25 | DMSO | 59 |
| 16B | —OCH₂CH₂OCH₃ | 24 | 25 | DMSO | 90 |
| 17B | —OCH₂CH₂N(CH₃)₂ | 24 | 25–45 | DMSO | 65 |

| Example No. | MOLECULAR FORMULA | | ELEMENTAL ANALYSIS | | | | |
|---|---|---|---|---|---|---|---|
| | | | C | H | Cl | F | N |
| 8B | C₁₆H₁₁ClF₃NO₅ | THEORY | 49.31 | 2.84 | 9.09 | 14.63 | 3.59 |
| | | FOUND | 49.70 | 2.96 | 8.85 | 14.15 | 3.30 |
| 11B | C₁₇H₁₃ClF₃NO₅ | THEORY | 50.57 | 3.24 | 8.78 | 14.17 | 3.47 |
| | | FOUND | 50.85 | 3.50 | 8.70 | 13.70 | 3.35 |
| 12B | C₁₇H₁₃ClF₃NO₅ | THEORY | 50.57 | 3.24 | 8.78 | 14.17 | 3.47 |
| | | FOUND | 50.56 | 3.26 | 8.96 | 14.41 | 3.41 |
| 13B | C₁₈H₁₅ClF₃NO₅ | THEORY | 51.75 | 3.61 | 8.48 | 13.64 | 3.35 |
| | | FOUND | 51.87 | 3.86 | 8.47 | 13.52 | 3.13 |

TABLE IV-continued $$CF_3\text{-}\underset{Cl}{\text{Ar}}\text{-}OH + F\text{-}\underset{COR^{11}}{\text{Ar}}\text{-}NO_2 \xrightarrow{K_2CO_3} CF_3\text{-}\underset{Cl}{\text{Ar}}\text{-}O\text{-}\underset{COR^{11}}{\text{Ar}}\text{-}NO_2$$

|     | Formula | | C | H | Cl | F/N | N |
| --- | --- | --- | --- | --- | --- | --- | --- |
| 14B | $C_{22}H_{23}ClF_3NO_5$ | THEORY | 55.75 | 4.88 | 7.48 | 12.03 | 2.97 |
|     |  | FOUND | 56.14 | 5.10 | 7.58 | 11.48 | 2.76 |
| 15B | $C_{16}H_{11}ClF_3NO_6$ | THEORY | 47.36 | 2.73 | 8.73 | 14.04 | 3.05 |
|     |  | FOUND | 47.10 | 2.72 | 8.58 | 16.99 | 3.29 |
| 16B | $C_{16}H_{11}ClF_3NO_6$ | THEORY | 48.64 | 3.12 | 8.44 | 13.57 | 3.33 |
|     |  | FOUND | 48.40 | 3.23 | 8.68 | 13.18 | 3.17 |
| 17B | $C_{18}H_{16}ClF_3N_2O_5$ | THEORY | 49.95 | 3.73 | 8.19 | 13.17 | 6.47 |
|     |  | FOUND | 48.86 | 3.69 | 8.14 | 13.59 | 6.16 |

EXAMPLE 18B 5-(2-Chloro-4-trifluoromethylphenoxy)-2-nitrobenzamide

To a 100 ml flask fitted with a magnetic stirrer and drying tube is added dimethyl sulfoxide (50 ml), anhydrous potassium carbonate (3.6 g, 0.026 mole) and 2-chloro-4-trifluoromethylphenol (4.8 g, 0.024 mole). This mixture is stirred at room temperature overnight. 5-Fluoro-2-nitrobenzamide (4.5 g, 0.024 mole) is added rapidly and the reaction mixture stirred at room temperature for 24 hours. The reaction mixture is poured into water (300 ml) and triturated with carbon tetrachloride (50 ml). The water and carbon tetrachloride insoluble solid is collected by filtration and dried under vacuum to afford 1.2 g of 5-(2-chloro-4-trifluoromethylphenoxy)-2-nitrobenzamide, mp 139°–43° C. Anal. Calcd. for $C_{14}H_8ClF_3N_2O_4$: C, 46.62; H, 2.23; Cl, 9.83; N, 7.76. Found: C, 45.77; H, 2.30; Cl, 10.62; N, 7.91.

EXAMPLE 19B

N,N-Diethyl-5-(2-Chloro-4-trifluoromethylphenoxy)-2-nitrobenzamide

To a 100 ml flask fitted with a magnetic stirrer and drying tube is added dimethyl sulfoxide (30 ml), anhydrous potassium carbonate (7.55 g, 0.054 mole) and 2-chloro-4-trifluoromethylphenol (10.3 g, 0.052 mole). The mixture is stirred at room temperature overnight. A solution of N,N-diethyl-5-fluoro-2-nitrobenzamide (12.5 g, 0.052 mole) in dimethyl sulfoxide (20 ml) is then added rapidly and the reaction mixture is stirred at room temperature for 60 hours. The reaction mixture is poured into water (500 ml) and the product extracted into carbon tetrachloride (4×100 ml), the combined extracts are dried over anhydrous magnesium sulfate and the solvent removed under vacuum to afford 15.3 g of 5-(2-chloro-4-trifluoromethylphenoxy)-2-nitrobenzamide (75% yield) Recrystallization from benzene/hexane affords substantially pure product mp. 75°–79° C. Elemental anal, Calcd. for $C_{18}H_{16}ClF_3N_2O_4$: C, 51.80; H, 3.88; Cl, 8.55; F, 13.68; N, 6.73. Found: C, 52.03; H, 3.90; Cl, 8.54; F, 13.59; N, 6.83.

EXAMPLE 20B

Methyl 5-(2-Chloro-4-trifluoromethylphenoxy)-2-nitrobenzoate

To a flask fitted with a drying tube is charged DMSO (10 ml), 2-chloro-4-trifluoromethylphenol (3.93 g, 0.02 mole) and anhydrous potassium carbonate (2.76 g, 0.02 mole). Then methyl 5-chloro-2-nitrobenzoate (4.3 g, 0.02 mole) is added and the reaction mixture warmed to 50° C. for 3 hours. (Gas-liquid chromatography analysis suggested a low conversion to desired product.) The temperature is raised to 60° C. for 16 hours and then to 70° C. for 16 hours. Additional potassium carbonate (1.38 g, 0.01 mole) is added and heating at 70° C. is continued for an additional 5 days, the reaction mixture is cooled to room temperature, poured into a benzene/hexane cosolvent and extracted twice with water. The organic layer is dried with anhydrous sodium sulfate, filtered and the solvent removed under vacuum (110° C., 0.1 mm) to afford 2.0 g, (27% yield) of methyl 5-(2-chloro-4-trifluoromethylphenoxy)-2-nitrobenzoate which is determined by spectral data to be identical with the product of Example 1B.

EXAMPLE 21B

Methyl 5-(2-Chloro-4-trifluoromethylphenoxy)2-nitrobenzoate

Similarly to Example 20B, tetrahydrothiophene 1,1-dioxide is substituted for DMSO and the reaction temperature was maintained at 115° C. for 24 hours to afford 2 g of methyl 5-(2-chloro-4-trifluoromethylphenoxy)-2-nitrobenzoate.

EXAMPLE 22B

Methyl 5-(2-Chloro-4-trifluoromethylphenoxy)-2-nitrobenzoate

The potassium salt of 2-chloro-4-trifluoromethylphenol is prepared by adding, at 0°–5° C., one equivalent of 2-chloro-4-trifluoromethylphenol to a solution of 1 equivalent of potassium hydroxide dissolved in methanol. The solvent is removed under vacuum and tetrahydrothiophene 1,1-dioxide is added to dissolve the anhydrous potassium salt (II). This solution is then added dropwise to 1 equivalent of methyl 5-chloro-2-nitrobenzoate dissolved in tetrahydrothioxene 1,1-dioxide preheated to 105° C. Upon completion of addition the temperature is raised to 125° C. for 3 hours, then cooled to room temperature, poured into water and extracted into carbon tetrachloride. GLC analysis suggests that the yield is comparable to Example 21B.

By following the general procedures of Examples 1B, 18B, 19B or 20B and selecting the appropriate 4-trifluoromethylphenol (IIa) and halonitrobenzene (III) there can also be prepared the compounds (I) illustrated in Table V:

TABLE V

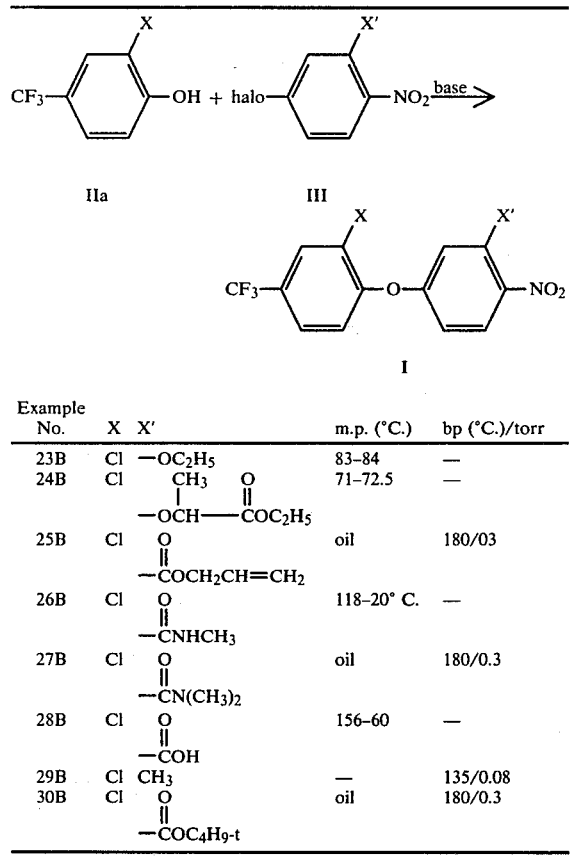

| Example No. | X | X' | m.p. (°C.) | bp (°C.)/torr |
|---|---|---|---|---|
| 23B | Cl | —OC₂H₅ | 83–84 | — |
| 24B | Cl | —OCH(CH₃)—COC₂H₅ (O) | 71–72.5 | — |
| 25B | Cl | —COCH₂CH=CH₂ (O) | oil | 180/03 |
| 26B | Cl | —CNHCH₃ (O) | 118–20° C. | — |
| 27B | Cl | —CN(CH₃)₂ (O) | oil | 180/0.3 |
| 28B | Cl | —COH (O) | 156–60 | — |
| 29B | Cl | CH₃ | — | 135/0.08 |
| 30B | Cl | —COC₄H₉-t (O) | oil | 180/0.3 |

The product of Example 28B can also be prepared by acid or base catalyzed ester hydrolysis of Examples 1B or 8B–17B and the like, one illustration of which is depicted in Example 31B:

EXAMPLE 31B 5-(2-Chloro-4-trifluoromethylphenoxy)-2-nitrobenzoic acid

Ethyl 5-(2-chloro-4-trifluoromethylphenoxy)-2-nitrobenzoate (Example 8B, 20 g., 0.058 mole) is dissolved in ethanol (20 g) and a solution of 50% aqueous sodium hydroxide (9.6 g, 4 g, 0.120 mole) is added dropwise beginning at 25° C. The rate of addition is adjusted so as to control the exothermic reaction at less than or equal to 52° C. By this method the sodium salt of 5-(2-chloro-4-trifluoromethylphenoxy)-2-nitrobenzoic acid is generated in situ. Treatment with 6 M HCl to pH 1 in water (100 ml) affords the free acid as a heavy oil which is extracted into ethylene chloride. The ethylene chloride layer is decanted and concentrated under vacuum to afford 17.6 g of a thick brown syrupy material which crystallizes upon further trituration with ethylene dichloride as an off-white powder, mp 156°–60° C. which is identified by spectral means to be 5-(2-chloro-4-trifluoromethylphenoxy)-2-nitrobenzoic acid.

By standard chemical methods 5-(2-chloro-4-trifluoromethylphenoxy)-2-nitrobenzoic acid can be converted to agronomically acceptable alkali and alkaline earth metal salts by reaction with one equivalent of an appropriate metal hydroxide or to agronomically acceptable amine salts by combining the acid with one equivalent of the appropriate amine. Solutions of the acid salts or free salts can be obtained depending upon reaction conditions. One method, not meant to be limiting but rather exemplary, to isolate the sodium salt is described in Example 32B.

EXAMPLE 32B

Sodium 5-(2-Chloro-4-trifluoromethylphenoxy)2-nitrobenzoate 5-(2-chloro-4-trifluoromethylphenoxy)-2-nitrobenzoic acid (3.0 g, 0.0083 mole) is dissolved in iso-propyl alcohol (20 ml) and a solution of 50% aqueous sodium hydroxide (0.644 g, 0.0083 mole) is added dropwise and the reaction mixture stirred for 1 hour before removing the solvent and water under vacuum at 0.2 mm overnight to afford 2.8 g of sodium 5-(2-chloro-4-trifluoromethylphenoxy)-2-nitrobenzoate.

EXAMPLE 33B

Methyl 5-(4-Chloro-2-trifluoromethylphenoxy)2-nitrobenzoate

To a flask is added DMSO (10 ml) 4-chloro-2-trifluoromethylphenol (3.0 g, 0.015 mole), anhydrous potassium carbonate (2–5 g, 70.015 mole) and methyl 5-fluoro-2-nitrobenzoate (2.99 g, 0.015 mole). The reaction mixture is stirred at room temperature for 7 hours, poured in water (150 ml) and then triturated with CCl₄ (50 ml then 35 ml) and the organic layer decanted and removed under vacuum to afford 5.3 g of product as a yellow oil. Elemental anal. calcd. for $C_{15}H_9ClF_3NO_5$: C, 47.90; H, 2.42; Cl, 9.68; F, 15.20; N, 3.73. Found: C, 47.70; H, 2.49; Cl, 9.61; F, 14.89; N, 3.31.

What is claimed:

1. A process for preparing a compound of the formula

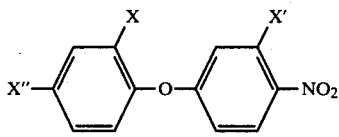

wherein X is hydrogen, halo, trifluoromethyl or lower alkyl; X' is hydrogen, halo, cyano, lower alkyl, lower alkoxy, carboxy, carbalkoxy, carbalkoxyalkoxy, alkoxycarbalkoxy, carbalkenyloxy, carbamoyl, mono- and dialkylcarbamoyl or trifluoromethyl, and X" is halo or trifluoromethyl with the proviso that when X" is halo X is trifluoromethyl, which comprises treating a compound of the formula:

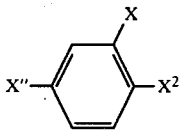

wherein X and X" are as defined above and $X^2$ is fluoro or chloro with an alkali or alkaline earth metal hydroxide at a temperature in the range of from about 50° to about 100° C. for a period of time in the range from 5 hour to about 5.5 days in a solvent system comprising a dipolar, aprotic solvent having a dielectric constant in the range of from about 30 to about 70, said solvent being inert or substantially inert to said hydroxide, and a non-nucleophilic, hydroxylated cosolvent that increases the solubility of hydroxide to afford a trifluoromethylphenate of the formula

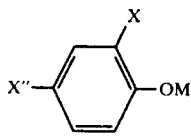

wherein X and X'' are is as defined above and M is an alkali metal or alkaline earth metal cation, which may be isolated upon acidification as the free phenol or reacted with a halonitrobenzene of the formula:

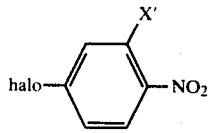

wherein X' is as defined above and halo is fluoro or chloro in a dipolar, apiotic solvent at temperatures ranging from 20°–130° C. for halo being fluoro and from 50°–130° C. for halo being chloro for a period of from one hour to six days depending upon the nature of M, halo, X and X'.

2. The process of claim 1 for preparing a compound of the formula

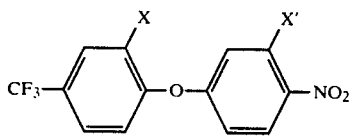

wherein X and X' are as defined in claim 1 which comprises treating a compound of the formula:

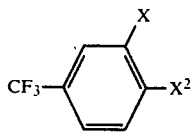

wherein X and $X^2$ are as defined in claim 1 with an alkali metal or alkaline metal hydroxide in a solvent system comprising a non-nucleophilic hydroxy containing solvent and a dipolar, aprotic solvent selected from dimethylsulfoxide tetrahydrothiophene-1,1-dioxide or hexamethylphosphoric triamide to afford a compound of the formula

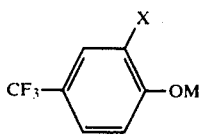

wherein X and M are as defined in claim 1 and then treating said compound with a halobenzene of the formula

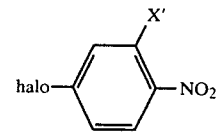

wherein X' is as defined above at a temperature in the range of from about 20° to 130° C. in a dipolar, aprotic solvent selected from dimethyl sulfoxide, dimethylformamide, N-methylacetamide, tetrahydrothiophene 1,1-dioxide, hexamethylphosphoric triamide, 1,4-dioxane, ethylene carbonate or 1,2-dimethoxyethane.

3. The process of claim 2 wherein the non-nucleophilic hydroxy containing compound is selected from among

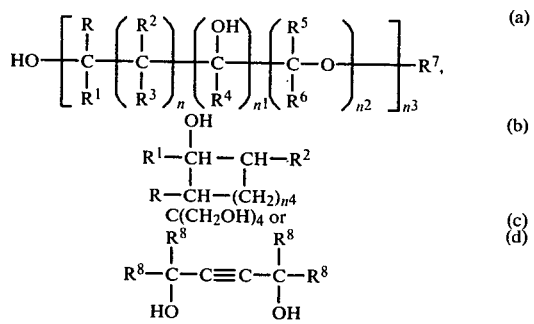

wherein R, $R^1$, $R^2$, $R^3$, $R^4$, $R^5$, $R^6$ and $R^7$ are the same or different groups selected from hydrogen; straight or branched lower alkyl, substituted or unsubstituted phenyl substituents wherein phenyl substituents may be alkyl, halo, lower alkoxy, a benzyl, and the like; $R^8$ is lower alkyl; n and $n^2$ are 0 or 1; $n^1$ is 0 to 2, $n^3$ is an integer of from 1 to 10; $n^4$ is 2 to 4 provided that $n^1$ is 2 only when n and $n^2$ are both 0, otherwise the sum of $n^1$ and $n^2$ may not simultaneously be greater than 1; when $n^3$ is greater than 2, the sum of n and $n^2$ may not simultaneously be greater than 1 and $n^1$ must be 0; when $R^7$ is hydrogen, n' must be zero and the sum of n and $n^2$ must be 1 such that at least 3 of the groups R, R' plus either the pair $R^2$ and $R^3$ or the pair of $R^5$ and $R^6$ must not be hydrogen.

4. The process of claim 3 wherein the hydroxy compound is selected from tert-butanol, pinacol, pentaeythritol, 2,4-dimethyl-2,4-pentanediol, 2,4-dimethyl-2,3,4-pentane triol, 2,4-dimethyl-3-pentanol, 2,2,2-trimethyl-3-pentanol, 2,2-dimethyl-1-propanol, 2,5-dimethyl-3-hexane-2,5-diol, 1-methyl-1-cyclohexanol or 2-isopropyl-1-cyclopentanol.

5. The process of claim 2 wherein the solvents are employed in the ratio of from about 1 part to about 30 parts of the non-nulceophilic hydroxy solvent to about 100 parts of the dipolar, aprotic solvent.

6. The process of claim 5 wherein the solvents are employed in the ratio of from about 5 to about 20 parts of the non-nucleophilic hydroxy solvent to about 100 parts of the dipolar, aprotic solvent.

7. The process of claim 2 wherein X is chloro, X' is hydrogen, methoxy, ethoxy, carboxy, methoxyethoxycarbonyl, methoxycarbonyl, ethoxycarbonyl, allyloxycarbonyl, sodium carboxylate or potassium carboxylate.

8. The process of claim 7 wherein X' is sodium carboxylate.

9. The process of claim 7, wherein X' is potassium carboxylate.

10. The process of claim 7, wherein X' is methoxycarbonyl.

11. The process of claim 7 wherein X' is ethoxycarbonyl.

12. The process of claim 7 wherein X' is methoxyethoxycarbonyl.

* * * * *